United States Patent [19]

Yokoshima et al.

[11] Patent Number: 4,843,111
[45] Date of Patent: Jun. 27, 1989

[54] DIESTERS OF (METH)ACRYLIC ACID AND RESIN COMPOSITIONS COMPRISING THE SAME

[75] Inventors: Minoru Yokoshima, Yamaguchi; Tetsuo Ohkubo, Ube; Hideaki Hattori, Yono; Masayuki Kiyomoto, Yamaguchi, all of Japan

[73] Assignee: Nippon Kayaku Kabushiki Kaisha, Tokyo, Japan

[21] Appl. No.: 41,072

[22] PCT Filed: Sep. 12, 1985

[86] PCT No.: PCT/JP85/00509
§ 371 Date: Jan. 21, 1987
§ 102(e) Date: Jan. 21, 1987

[87] PCT Pub. No.: WO87/01697
PCT Pub. Date: Mar. 26, 1987

[51] Int. Cl.$^4$ .............................. C08F 2/50; C08F 20/20
[52] U.S. Cl. .............................. 522/42; 522/43; 522/44; 522/45; 522/48; 522/53; 522/91; 522/92; 522/93; 522/94; 522/95; 522/96; 522/103; 350/96.29; 560/185
[58] Field of Search .................. 526/96, 282; 523/466; 522/77, 33, 42–48, 53, 90–96, 103; 560/185

[56] References Cited

U.S. PATENT DOCUMENTS 4,323,696 4/1987 Schmitz-Josten et al. ......... 526/282

FOREIGN PATENT DOCUMENTS 1198083 12/1985 Canada ............................ 204/91.49
58-51011 11/1983 Japan .

Primary Examiner—John C. Bleutge
Assistant Examiner—A. H. Koeckert
Attorney, Agent, or Firm—Birch, Stewart, Kolasch & Birch

[57] ABSTRACT

Disclosed herein are novel diesters of (meth)acrylic acid represented by the following formula:

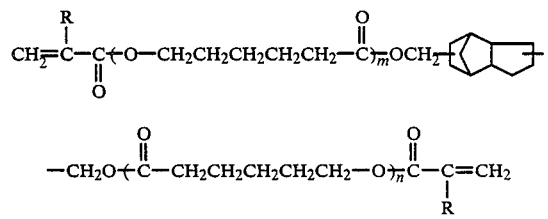

wherein the mean values of m and n are respectively 0 to 5, preferably 0 to 3, the mean value of m+n is 1 to 10, preferably 1 to 6, and R represents H or $CH_3$.

Also, disclosed herein are resin compositions comprising said diester(s) of (meth)acrylic acid, polyurethane (meth)acrylate(s), monoethylenically unsaturated monomer(s) and initiator(s) of photopolymerization as an optional component.

14 Claims, No Drawings

DIESTERS OF (METH)ACRYLIC ACID AND RESIN COMPOSITIONS COMPRISING THE SAME

INDUSTRIAL FIELD OF UTILIZATION

The present invention relates to novel diester of (meth)acrylic acid, which can be copolymerized easily with each of the resins containing unsaturated group(s) in the presence of heat, ultraviolet ray, ionizing radiation or a radical-initiator, and resins comprising the same.

BACKGROUND OF THE INVENTION

The range of the use of optical fiber has been remarkably increased in recent years, particularly in the field of communications, because the information-transmitting capacity of optical fiber is large and optical fiber is relatively free from intervention from outside. Since optical fiber is used in the field of communication, it is generally made of glass. However, glass fiber is brittle and is chemically attacked by water vapour, and accordingly, it is easily broken and is handled with difficulty. Therefore, the surface of optical glass fiber has hitherto been coated with a resin.

As a resinous coating material for such a purpose, epoxy resin, urethane resin and the like have been hitherto used, however, since they are poor in productivity because of the necessity of a long term for curing them and they lack pliability, they have a disadvantage in the transmission specificity of the optical glass fiber coated therewith is reduced by side pressure. For the purpose of improving the above-mentioned disadvantage, the compositions containing urethane acrylate, which are curable by ultraviolet rays, have been actively investigated recently, and such a composition for optical glass fiber and a method for forming a coating have been proposed, for instance, in Japanese Patent Applications Laid-Open (KOKAI) No. 58-223638 (1983) and No. 59-170154 (1984).

In these patent applications, a primary coating of a very low modulus has been used for solving the above-mentioned problem, and a considerable success has been obtained thereby. However, for providing the low modulus, the strength and hardness necessitated to the coating on the surface of glass have been sacrificed, and accordingly, it is desirable to form a top coating onto the primary coating. Compositions for the top coating, which are curable by ultraviolet rays, have been investigated. For instance, a composition for a top coating curable by ultraviolet rays is proposed in Japanese Patent Application Laid-Open (KOKAI) No. 59-170155 (1984).

PROBLEMS TO BE SOLVED BY THE INVENTION

The top coating composition curable by ultraviolet rays which is now in use has merits in that the curing speed thereof is high and that the desired properties for coating are easily and exactly obtainable, however, such a composition has disadvantages in that the glass fiber is apt to be attacked by water because of large degree of water-absorption of the coating and the fiber is broken in the rolling up step of process because of low elongation of the cured coating.

MEANS FOR SOLVING THE PROBLEMS

The present invention provides novel diesters of (meth)acrylic acid applicable for various uses and novel resin compositions which have a high curing speed and are suitable for top-coating of the optical glass fiber for transmission by light, the elongation of the resinous coating obtained by curing the composition being large and the degree of water-absorption of the resinous coating being small.

Namely, the present invention relates to (1) diesters of (meth)acrylic acid represented by the formula (I):

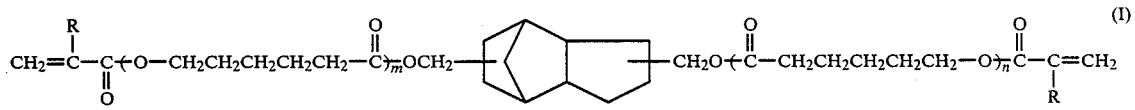

wherein the mean values of m and n are respectively 0 to 5, preferably 0 to 3; the mean value of m+n is 1 to 10, preferably 1 to 6 and R is a hydrogen atom or a methyl group, and (2) resin compositions comprising (A) polyurethane (meth)acrylate(s), (B) diester(s) of (meth)acrylic acid represented by the formula (I):

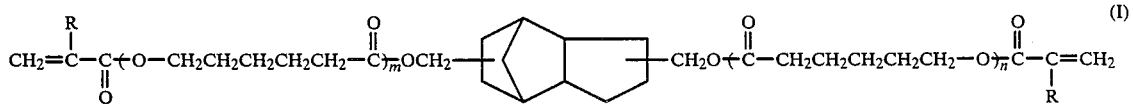

wherein the mean values of m and n respectively 0 to 5, preferably from 0 to 3; the mean value of m+n is 1 to 10, preferably 1 to 6 and R is a hydrogen atom or a methyl group, (C) a monoethylenically unsaturated monomer(s) and (D) initiator(s) of photopolymerization as an optional component.

The diester of (meth)acrylic acid represented by the formula (I) is available by esterifying a compound represented by the formula (II):

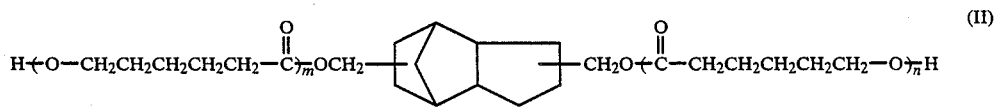

wherein m and n is respectively the same as in the formula (I), with acrylic acid or methacrylic acid.

The compound represented by the formula (II), namely, an adduct of tricyclodecanedimethylol and ε-caprolactone is produced by reaction of tricyclodecanedimethylol and ε-caprolactone as follows.

PRODUCTION OF AN ADDUCT (FORMULA (II)) OF TRICYCLODECANEDIMETHYLOL AND ε-CAPROLACTONE

During the reaction of tricyclodecanedimethylol and ε-caprolactone, it is preferable to use an effective amount of a catalyst, namely from 0.001 to 1.0 % by weight of ε-caprolactone, preferably from 0.01 to 0.2% by weight thereof. As examples of the catalysts, organic titanium compounds such as tetraisopropyl titanate, tetrabutyl titanate and the like, tin compounds such as tetraphenyltin, tetraoctyltin, dilauryltin oxide, di-n-butyltin dichloride and the like, etc. may be mentioned. The reaction of tricyclodecanedimethylol and ε-caprolactone is carried out at a temperature of 50° to 300° C., preferably 110° to 200° C. for a period sufficient for the completion of the reaction. The amount of ε-caprolactone used in the reaction is from about 1 to about 10 mol, preferably from 1 to 6 mol per one mol of tricyclodecanedimethylol used. In order to minimize the oxidative side reaction, it is preferable to carry out the reaction in the inert atmosphere such as gaseous nitrogen and the like. The reaction product comprising the adduct of tricyclodecanedimethylol and ε-caprolactone obtained as above can be utilized directly in the following esterification.

PRODUCTION OF A DIESTER OF (METH)ACRYLIC ACID (REPRESENTED BY FORMULA (I))

The diester of (meth)acrylic acid represented by the formula (I) is produced by subjecting the adduct of tricyclodecanedimethylol and ε-caprolactone represented by the formula (II) to reacting with acrylic acid, methacrylic acid or a mixture thereof. The amount of acrylic acid or methacrylic acid used in the reaction is from about 2 to about 4 mols per one mol of the adduct represented by the formula (II) used in the reaction.

Although it is desirable to subject the stoichiometrical amount, namely, 2 mols of acrylic acid, methacrylic acid or a mixture thereof to reacting with the active hydrogen atoms in the terminal hydroxyl groups of one mole of the adduct represented by the formula (II), actually, it is preferable to use an amount of acrylic acid or methacrylic acid a little more than the stoichiometrical amount thereof in order to carry out the reaction completely. It is preferable to carry out the reaction in the presence of a polymerization-inhibitor in order to minimize or retard the polymerization of acrylic compound(s). Such a polymerization-inhibitor has been well known by the persons skilled in the art, and is used in a concentration of 0.01 to 5% by weight of the reaction mixture. As an example of the polymerization-inhibitor, hydroquinone, p-methoxyphenol, 2,4-dimethyl-6-t-butylphenol, p-benzoquinone, phenothiazine, N-nitrosodiphenylamine, copper salts, etc. may be mentioned. The esterification reaction is generally carried out at a temperature of about 50° to 130° C., preferably 65° to 90° C. for a time period sufficient for completing the esterification. The period of carrying out the reaction depends on the scale of the reaction batch, the respective reactants, the catalyst and the reaction conditions adopted. In addition, a catalyst for esterification may be used in a concentration of 0.1 to 15 mol %, preferably 1 to 6 mol % of the amount of acrylic acid or methacrylic acid used in the reaction. For that purpose, any of the known catalyst for esterification may be used, and as an example thereof, p-toluenesulfonic acid, methanesulfonic acid, phosphoric acid, sulfuric acid, etc. may be mentioned. It is preferable in the esterification reaction to use an inert solvent such as hexane, cyclohexane, benzene and toluene to effect the removal of water formed during the esterification.

The thus produced diesters of (meth)acrylic acid are low in irritation, relatively low in viscosity and quickly cured, and can be applied in various uses after mixing with the other resins containing unsaturated group(s).

The composition containing the diester(s) of (meth)acrylic acid and resin(s) containing unsaturated group(s) can be cured by heat, ultraviolet ray, ionizing radiation, radical initiator, preferably by ultraviolet ray. In the case where the curing is carried out by ultraviolet ray, an initiator of photopolymerization is added to the composition at a concentration of 0.1 to 10% by weight of the composition. The initiator of photopolymerization has been well known and as an example thereof, benzyl ketal, benzoin isopropyl ether, benzophenone, thioxanthone, anthraquinone and etc. may be mentioned. As an example of the resin containing unsaturated group(s), which is usable together with the diester of (meth)acrylic acid, epoxy-acrylates such as acrylic acid ester of epoxidized bisphenol A, acrylic acid ester of epoxidized linseed oil and acrylic acid ester of epoxidized phenol novolak, unsaturated polyesters containing saturated or unsaturated carboxylic acid such as maleic acid, fumaric acid and adipic acid, and urethane acrylates obtained by reacting diisocyanates or polyisocyanates with hydroxyalkyl acrylates.

The composition containing the diester(s) of (meth)acrylic acid can be coated on the surface of any material such as wood, metal, glass, fabric, paper, fiber and plastics having an optional form, for instance, sheet, coil, molded article, film, panel, tube, etc.

The resin composition according to the present invention, which comprises (A) the polyurethane (meth)acrylate(s), (B) the diester(s) of (meth)acrylic acid represented by the formula (I), (C) monoethylenically unsaturated monomer(s) and (D) initiator(s) of photopolymerization as an optional component, is explained as follows.

The average molecular weight of the polyurethane (meth)acrylate (A) contained in the resin composition according to the present invention is ordinarily not less than 500, and preferably 500 to 5,000. As such a polyurethane (meth)acrylate, polyurethane (meth)acrylate of polyether polyol having ether linkage(s) in the molecule thereof, polyurethane (meth)acrylate of a carbonate polyol having carbonate linkage(s) in the molecule thereof, polyurethane (meth)acrylate of a polyester polyol having ester linkage(s) in the molecule thereof or polyurethane (meth)acrylate having both the ether linkage(s) and the ester linkage(s) may be mentioned. As the polyether polyol, for instance, polypropylene glycol, polyethylene glycol, polytetramethylene glycol and the compound formed by the addition of ethylene oxide or propylene oxide to 1,3-butylene glycol, 1,4-butylene glycol, 1,6-hexanediol, neopentyl glycol, cyclohexane dimethanol, 2,2-bis(4-hydroxycyclohexyl)-propane, bisphenol A and the like may be used. The polyester polyol can be obtained by reacting an alcoholic compound with an acidic compound. For instance, polypropylene glycol, polyethylene glycol, polytetramethylene glycol or a compound formed by the addition of ethylene oxide, propylene oxide or ε- caprolactone to 1,3-butylene glycol, 1,4-butylene glycol, 1,6-hexanediol, neopentyl glycol, cyclohexanedimethanol, 2,2-bis(4-hydroxycyclohexyl)propane, bisphenol A, and the like may be used as the alcoholic compound and, on the other hand, as the acidic compound, a dibasic acid such as phthalic acid, tetrahydrophthalic acid, adipic acid, sebacic acid, azelaic acid, hexahydrophthalic acid, dodecanedicarboxylic acid and an anhydride thereof may be used. In addition, also the compound obtained by reacting the alcoholic compound, acidic compound and ε-caprolactone simultaneously may be used as the polyester polyol.

The carbonate polyol can be produced, for instance, as follows.

Namely, the carbonate polyol is available by an esterexchange reaction of a carbonate derivative, for instance, a diaryl- or dialkyl carbonate such as diphenyl carbonate, bis(chlorophenyl) carbonate, dinaphthyl carbonate, phenyl toluyl carbonate, phenyl chlorophenyl carbonate, 2-tolyl 4-tolyl carbonate, dimethyl carbonate, diethyl carbonate and the like with a diol, for instance, 1,6-hexane diol, neopentyl glycol, 1,4-butanediol, 1,8-octanediol, 1,4-bis(hydroxymethyl)cyclohexane, 2-methylpropanediol, dipropylene glycol, dibutylene glycol or a polyester diol formed by reacting one of the diols with a dicarboxylic acid such as oxalic acid, malonic acid, succinic acid, adipic acid, azelaic acid, hexahydrophthalic acid and the like or ε-caprolactone. In addition, the carbonate polyol is available by the reaction of phosgen with one of the diols.

In order to obtain the polyurethane (meth)acrylate (A) while using the above polyether polyol, polycarbonate polyol or polyester polyol, an organic diisocyanate and a polymerizable monomer having hydroxyl group(s) are reacted with the hydroxyl group(s) of the polyol to the extent that the reaction product substantially does not contain any isocyanato group (—NCO). As the representative organic diisocyanate, aromatic diisocyanates such as tolylene diisocyanate, 4,4'-diphenylmethane diisocyanate and the like, alicyclic diisocyanates such as isophorone diisocyanate, 4,4'-dicyclohexylmethane diisocyanate and the like and aliphatic diisocyanates such as hexamethylene diisocyanate, 2,2'-trimethylhexamethylene diisocyanate and the like are exemplified, and as the polymerizable monomer having hydroxyl group(s), (meth)acrylates having a hydroxy group such as β-hydroxyethyl (meth)acrylate, δ-hydroxypropyl (meth)acrylate, β-hydroxylauryl (meth)acrylate, an adduct of ε-caprolactone and β-hydroxyethyl (meth)acrylate and the like are exemplified.

Although the reaction between the compound having —NCO and the compound having —OH proceeds in the absence of any catalyst, a conventional catalyst for the reaction of —NCO with —OH, for instance, tertiary amine such as triethyl amine and the like, organic metal compounds such as dibutyltin dilaurate, dibutyltin diacetate and the like or tin chlorides and the like may be used.

It is preferable to use the polyurethane (meth)acrylate (A) in an amount of 20 to 70% by weight of the amount of the resin composition, and particularly preferable to use in an amount of 30 to 60% by weight thereof.

The amount of the diester of (meth)acrylic acid (B) contained in the resin composition according to the present invention is preferably from 5 to 50% by weight of the resin composition, and particularly preferably from 20 to 40% by weight thereof.

Although as the monoethylenically unsaturated monomer (C) used in the resin composition according to the present invention various substances are utilizable, it is preferable to use the monomer which gives the homopolymer showing the glass-transition temperature as high as possible, and as an example, di-cyclopentadieneoxyethyl acrylate FA-512A, (made by HITACHI KASEI Co., Ltd.), dicyclopentadiene acrylate (FA-511A, made by HITACHI KASEI Co., Ltd.), hydrogenateddicyclopentadiene acrylate (FA-513A, made by HITACHI KASEI Co., Ltd.), isbornyl (meth)acrylate, (meth)acrylate of hydrogenated β-naphthol, (meth)acrylate of tricyclodecanemethylol, phenyloxyethyl (meth)acrylate, tetrahydrofurfuryl (meth)acrylate, adamanthane (meth)acrylate, N-vinylpyrrolidone, etc. may be mentioned.

Of the monoethylenically unsaturated monomers, hydrogenated-dicyclopentadiene acrylate (FA-513A, made by HITACHI KASEI Co., Ltd.) and dicyclopentadieneoxyethyl acrylate (FA-512A, made by HITACHI KASEI Co., Ltd.) are particularly preferable. The amount of the monoethylenically unsaturated monomer used according to the present invention is preferably from 10 to 50% by weight of the resin composition, particularly preferably from 20 to 40% by weight thereof.

The initiator of photopolymerization (D) contained in the resin composition according to the present invention as an optional component may be any one of the known initiator of photopolymerization, however, it is required that the initiator is excellent in stability after being compounded in the resin composition.

As such an initiator of photopolymerization, for instance, benzoin alkyl ethers such as benzoin ethyl ether, benzoin isobutyl ether, benzoin isopropyl ether, etc., acetophenones such as 2,2-diethoxyacetophenone, 4'-phenoxy-2,2-dichloroacetophenone, etc., propiophenones such as 2-hydroxy-2-methylpropiophenone, 4'-isopropyl-2-hydroxy-2-methylpropiophenone, 4'-dodecyl-2-hydroxy-2-methyl-propiophenone, etc., benzildimethylketal, 1-hydroxycyclohexyl phenyl ketone, anthraquinones such as 2-ethylanthraquinone and 2-chloroanthraquinone and thioxanthones may be mentioned. Of these initiators of photopolymerization (D), any one may be singly used or two or more of them may be used after mixing together at any ratio. The amount of the initiator used in the resin composition according to the present invention is usually not more than 10% by weight of the amount of the resin composition.

In the case where the resin composition according to the present invention is used as the material for coating the optical glass fiber, the initiator of photopolymerization (D) is an indispensable component of the resin composition, and in such a case, the amount of the initiator of photopolymerization in the resin composition is preferably from 0.1 to 10%, more preferably 1 to 5%, by weight of the amount of the resin composition.

In addition, polymerizable monomer(s) such as polyfunctional acrylate compounds such as polyethylene glycol di(meth)acrylate, polypropylene glycol di(meth)acrylate, trimethylolpropane triacrylate, etc., epoxyacrylate or polyester acrylate, etc. may be further added to the resin composition according to the present invention, if necessary. Further, resin(s) for modification and various kinds of adjuvant(s) may be added to the resin composition of the present invention. As the resin for modification, epoxy resins, polyurethanes, polybutadienes, polyethers, polyamideimides, silicone resins, phenol resins, etc. may be mentioned. As the adjuvant, organic silicon compounds, surfactants and polymerization-inhibitors may be mentioned.

Although the resin composition according to the present invention may be used for protective coating of plastic articles, it is particularly useful as a coating agent for the optical glass fiber. As the coating agent for the optical fiber glass, the resin composition according to the present invention is particularly useful as the top coating agent curable by ultraviolet rays, which is coated on the surface of the primary coating or the buffer coating on the surface of the optical fiber glass.

In the case where the resin composition according to the present invention is used as a coating agent for the optical glass fiber, the diesters of acrylic acid are preferable to the diesters of methacrylic acid as the component (B) in the resin composition.

As the method for coating in the case where the optical glass fiber is subjected to coating with the resin composition according to the present invention, the dies coating method is suitable, and in such a case, after wire-drawing the base material of the optical glass, a primary coating agent is coated thereonto and after curing the thus coated primary coating agent by irradiation of ultraviolet rays, the resin composition according to the present invention is coated as the top coating agent onto the primary coating at a preferable thickness of 20 to 300 μm.

The resin composition according to the present invention is easily cured by irradiation of ultraviolet rays, and such a curing of the resin composition according to the present invention by irradiation of ultraviolet rays may be carried out according to the conventional method. For instance, the thus coated resin composition is cured by irradiation of ultraviolet rays from a low-pressure mercury lamp, a high-pressure mercury lamp or a xenon lamp.

The present invention will be explained more in detail while referring to the non-limitative examples as follows, the part(s) in the examples being part(s) by weight.

EXAMPLES

Synthesis of an adduct of tricyclodecanedimethylol and $\epsilon$-caprolactone

SYNTHETIC EXAMPLE 1

In a 2 liter-reaction vessel equipped with a stirrer, a temperature controller, a thermometer and a reflux condenser, 942.2 parts of tricyclodecanedimethylol, 547.2 parts of $\epsilon$-caprolactone and 0.27 part of isopropyl titanate were introduced, and the mixture was heated to a temperature of 150° to 160° C. in a nitrogen atmosphere to carry out a reaction until the amount of unreacted $\epsilon$-caprolactone became less than 1% by weight. The thus obtained adduct was a pale yellow liquid of a hydroxy value of 360.5 and an acid value of 1.2. As a result of molecular weight determination, it was shown that the thus obtained adduct of tricyclodecanedimethylol and $\epsilon$-caprolactone had about one $\epsilon$-caprolactone unit in average in one molecule of the adduct.

SYNTHETIC EXAMPLE 2

In the same reactor as in Synthetic Example 1, 588.8 parts of tricyclodecanedimethylol, 684.8 parts of $\epsilon$-caprolactone and 0.34 part of stannous chloride were introduced, and the mixture was heated to a temperature of 110° to 120° C. in a nitrogen atmosphere to carry out the reaction until the amount of unreacted $\epsilon$-caprolactone became less than 1% by weight.

The thus obtained adduct was a pale yellow liquid of a hydroxy value of 266.5 and an acid value of 1.5. As a result of molecular weight determination, it was shown that the thus obtained adduct of tricyclodecanedimethylol and $\epsilon$-caprolactone had about 2 $\epsilon$-caprolactone units in one molecule of the adduct in average.

Synthesis of a diester of (meth)acrylic acid

EXAMPLE 1

In a 2-liter-reaction vessel equipped with a stirrer, a temperature controller, a thermometer, a reflux condenser and a separator, 470.3 parts of the 1:1 adduct of tricyclodecanedimethylol and $\epsilon$-caprolactone obtained in Synthetic Example 1, 262 parts of acrylic acid, 7.86 parts of sulfuric acid, 1.98 parts of hydroquinone, 364 parts of benzene and 90.6 parts of cyclohexane were introduced, and the mixture was heated to a temperature of 81° to 89° C., thereby carrying out the reaction. The formed water was distilled together with the solvent, condensed and removed to out side the reaction system while the condensed and separated solvent were returned to the reaction vessel. When 54.6 parts of water were formed, the reaction mixture was cooled. After dissolving the reaction mixture in 809 parts of benzene and 202.4 parts of cyclohexane and neutralizing the solution with an aqueous 20% solution of sodium hydroxide, the neutralized solution was washed three times with each 500 parts of an aqueous 20% solution of sodium chloride. By distilling the solvent off from the thus washed solution under a reduced pressure, 523.4 parts of a pale yellow liquid showing the following properties were obtained.

| specific gravity (25° C.) | 1.105 | |
|---|---|---|
| viscosity (25° C.) | 241.7 cps | |
| saponification value | 401.3 mgKOH/g | |
| acid value | 0.02 mgKOH/g | |
| refractive index (20° C.) | 1.4975 | |
| Elementary analytical data | C (%) | H (%) |
| | 68.89 | 8.20 |

The result of measurement of absorption spectrum of high resolution nuclear magnetic resonance (NMR) is shown below.

| No. of Peak | Absorption frequency (Hz) | No. of Peak | Absorption frequency (Hz) |
|---|---|---|---|
| 1 | 11739.6 | 25 | 2809.3 |
| 2 | 11246.0 | 26 | 2789.5 |
| 3 | 8831.1 | 27 | 2747.6 |
| 4 | 8703.3 | 28 | 2738.8 |
| 5 | 5263.8 | 29 | 2725.6 |
| 6 | 5233.0 | 30 | 2663.9 |
| 7 | 5200.0 | 31 | 2633.0 |
| 8 | 4662.3 | 32 | 2586.8 |
| 9 | 4651.3 | 33 | 2309.1 |
| 10 | 4622.7 | 34 | 2254.0 |
| 11 | 4594.0 | 35 | 2214.4 |
| 12 | 4587.4 | 36 | 2205.6 |
| 13 | 4349.5 | 37 | 2086.6 |
| 14 | 4334.0 | 38 | 2060.2 |
| 15 | 3366.7 | 39 | 1983.0 |
| 16 | 3318.3 | 40 | 1916.9 |
| 17 | 3089.1 | 41 | 1901.5 |
| 18 | 3040.6 | 42 | 1883.9 |
| 19 | 3016.4 | 43 | 1853.0 |
| 20 | 3001.0 | 44 | 1727.4 |
| 21 | 2967.9 | 45 | 1705.4 |
| 22 | 2912.9 | 46 | 1663.5 |

-continued

| No. of Peak | Absorption frequency (Hz) | No. of Peak | Absorption frequency (Hz) |
| --- | --- | --- | --- |
| 23 | 2895.2 | 47 | 1656.9 |
| 24 | 2826.9 | | |

In the NMR determination, tetramethylsilane was used as the standard substance, and chloroform was used as the solvent for the specimen, and after carrying out the determination of $^1$H signals and $^{13}$C-H coupling signals $^{13}$C-D coupling signals were determined to obtain identification results. Of the absorptions, Nos. 5, 6 and 7 show the absorption by the solvent.

EXAMPLE 2

In the same reaction vessel as used in Example 1, 509.5 parts of the 1:2 adduct of tricyclodecanedimethylol and ε-caprolactone obtained in Synthetic Example 2, 207.4 parts of acrylic acid, 6.2 parts of sulfuric acid, 1.6 parts of hydroquinone, 384 parts of benzene and 96 parts of cyclohexane were introduced, and the reaction was carried out at a temperature of 80° to 87° C. in the same manner as in Example 1 until 57.6 parts of water were formed. After dissolving the reaction mixture in 1065 parts of benzene and 266.3 parts of cyclohexane, and neutralizing the solution with an aqueous 20% solution of sodium hydroxide, the thus neutralized solution was washed three times with each 400 parts of an aqueous 20% solution of sodium chloride. By distilling the solvent off from the thus washed solution under a reduced pressure, 743.1 parts of a pale yellow liquid were obtained. The liquid showed the following properties.

| | | |
| --- | --- | --- |
| specific gravity (25° C.) | 1.102 | |
| viscosity (25° C.) | 419.2 cps | |
| saponification value | 420.9 mgKOH/g | |
| acid value | 0.04 mgKOH/g | |
| refractive index (20° C.) | 1.4925 | |
| Elementary analytical data: | C (%) | H (%) |
| | 67.66 | 8.32 |

The results of NMR measurement are as follows.

| No. of Peak | Absorption frequency (Hz) | No. of Peak | Absorption frequency (Hz) |
| --- | --- | --- | --- |
| 1 | 11732.9 | 22 | 2824.7 |
| 2 | 11239.4 | 23 | 2809.3 |
| 3 | 8828.9 | 24 | 2787.3 |
| 4 | 8701.1 | 25 | 2738.8 |
| 5 | 5263.8 | 26 | 2725.6 |
| 6 | 5233.0 | 27 | 2661.7 |
| 7 | 5200.0 | 28 | 2630.8 |
| 8 | 4662.3 | 29 | 2586.8 |
| 9 | 4620.5 | 30 | 2304.7 |
| 10 | 4607.2 | 31 | 2254.0 |
| 11 | 4585.2 | 32 | 2214.4 |
| 12 | 4349.5 | 33 | 2086.6 |
| 13 | 4334.0 | 34 | 2060.2 |
| 14 | 3357.9 | 35 | 1983.0 |
| 15 | 3316.1 | 36 | 1916.9 |
| 16 | 3089.1 | 37 | 1883.9 |
| 17 | 3038.4 | 38 | 1857.4 |
| 18 | 3016.4 | 39 | 1727.4 |
| 19 | 2967.9 | 40 | 1705.4 |
| 20 | 2912.9 | 41 | 1661.3 |
| 21 | 2895.2 | 42 | 0.0 |

Of the absorptions shown above, Nos, 5 and 7 are the absorption peaks of the solvent.

EXAMPLE 3

According to the same procedure as in the Synthetic Examples, an adduct of tricyclodecanedimethylol and ε-caprolactone having about four ε-caprolactone units in average in one molecule thereof was synthesized, and after introducing 502.8 parts of the thus synthesized adduct, 133.2 parts of acrylic acid, 4.0 parts of sulfuric acid, one part of phenothiazine, 384 parts of benzene and 96 parts of cyclohexane into the same reaction vessel as in Example 1, the reaction was carried out at a temperature of 80° to 88° C. in the same manner as in Example 1 until 27.7 parts of water were formed.

After dissolving the reaction mixture in 720 parts of benzene and 180 parts of cyclohexane, neutralizing the solution with an aqueous 20% solution of sodium hydroxide, the thus neutralized solution was washed three times with each 400 parts of an aqueous 20% solution of sodium chloride. By distilling the solvent off from the thus washed solution under a reduced pressure, 510.9 parts of a pale yellow liquid were obtained. The thus obtained liquid showed the following properties.

| | | |
| --- | --- | --- |
| specific gravity (25° C.) | 1.0985 | |
| viscosity (25° C.) | 561.3 cps | |
| saponification value | 441.3 mgKOH/g | |
| acid value | 0.02 mgKOH/g | |
| refractive index (20° C.) | 1.4879 | |
| Elementary analytical data | C (%) | H (%) |
| | 66.31 | 8.49 |

The result of NMR measurement:

| No. of Peak | Absorption frequency (Hz) | No. of Peak | Absorption frequency (Hz) |
| --- | --- | --- | --- |
| 1 | 11735.1 | 24 | 2899.6 |
| 2 | 11241.6· | 25 | 2826.9 |
| 3 | 8831.1 | 26 | 2809.3 |
| 4 | 8703.3 | 27 | 2789.5 |
| 5 | 5268.3 | 28 | 2756.4 |
| 6 | 5235.2 | 29 | 2738.8 |
| 7 | 5202.2 | 30 | 2727.8 |
| 8 | 4684.4 | 31 | 2663.9 |
| 9 | 4651.3 | 32 | 2633.0 |
| 10 | 4622.7 | 33 | 2589.0 |
| 11 | 4609.4 | 34 | 2306.9 |
| 12 | 4587.4 | 35 | 2256.2 |
| 13 | 4349.5 | 36 | 2212.2 |
| 14 | 4336.2 | 37 | 2088.8 |
| 15 | 3360.1 | 38 | 2060.2 |
| 16 | 3349.1 | 39 | 1985.2 |
| 17 | 3316.1 | 40 | 1916.9 |
| 18 | 3089.1 | 41 | 1886.1 |
| 19 | 3040.6 | 42 | 1859.6 |
| 20 | 3016.4 | 43 | 1727.4 |
| 21 | 3001.0 | 44 | 1707.6 |
| 22 | 2970.1 | 45 | 1663.5 |
| 23 | 2915.1 | 46 | 0.0 |

Of the absorptions shown above, Nos. 5, 6 and 7 are the absorption peaks of the solvent.

EXAMPLE 4

After synthesizing an adduct of ε-tricyclodecanedimethylol and ε-caprolactone having about 10 ε-caprolactone units in average in one molecule of the adduct according to the same procedure as in the Synthetic Examples, 642.3 parts of the thus synthesized adduct, 72.6 parts of acrylic acid, 7.5 parts of p-toluenesulfonic acid, 0.6 parts of phenothiazine, 560 parts of benzene and 140 parts of cyclohexane were introduced into the same reaction vessel as in Example 1. The reaction was carried out at a temperature of 81° to 88° C. in the same manner as in Example 1 until 17.2 parts of water were formed. After dissolving the reaction mixture in 800 parts of benzene and 200 parts of cyclohexane, neutralizing the solution with an aqueous 20% solution of sodium hydroxide, and washing the thus neutralized solution three times with each 400 parts of an aqueous 20% solution of sodium chloride, the solvent in the solution was distilled off from the solution under a reduced pressure, thereby obtaining 539.1 parts of a pale yellow semi-solid substance showing the following properties.

| acid value | 0.02 mgKOH/g | |
|---|---|---|
| saponification value | 465.1 mgKOH/g | |
| Elementary analytical data: | C (%) | H (%) |
| | 64.75 | 8.65 |

The result of NMR measurement:

| No. of Peak | Absorption frequency (Hz) | No. of Peak | Absorption frequency (Hz) |
|---|---|---|---|
| 1 | 11739.6 | 22 | 2899.6 |
| 2 | 11243.8 | 23 | 2809.3 |
| 3 | 8833.3 | 24 | 2787.3 |
| 4 | 8701.1 | 25 | 2725.6 |
| 5 | 5261.6 | 26 | 2663.9 |
| 6 | 5230.8 | 27 | 2630.8 |
| 7 | 5197.7 | 28 | 2591.2 |
| 8 | 4684.4 | 29 | 2306.9 |
| 9 | 4651.3 | 30 | 2254.0 |
| 10 | 4585.2 | 31 | 2212.2 |
| 11 | 4351.7 | 32 | 2187.9 |
| 12 | 4336.2 | 33 | 2088.8 |
| 13 | 4261.3 | 34 | 2055.7 |
| 14 | 4221.7 | 35 | 1916.9 |
| 15 | 3346.9 | 36 | 1883.9 |
| 16 | 3313.9 | 37 | 1859.6 |
| 17 | 3086.9 | 38 | 1727.4 |
| 18 | 3038.4 | 39 | 1661.3 |
| 19 | 3016.4 | 40 | 1474.1 |
| 20 | 2967.9 | 41 | 0.0 |
| 21 | 2915.1 | | |

Of the absorptions shown above, Nos. 5, 6 and 7 are absorption peaks of the solvent.

EXAMPLE 5

After synthesizing an adduct of tricyclodecanedimethylol and ε-caprolactone having about 4 ε-caprolactone units in average in one molecule of the adduct according to the same procedure as in the Synthetic Examples, 502.8 parts of the thus synthesized adduct, 159.1 parts of methacrylic acid, 4.0 parts of sulfuric acid, 0.5 part of hydroquinone, 0.5 part of phenothiazine and 470 parts of toluene were introduced into the same reaction vessel as in Example 1, and the reaction was carried out at a temperature of 108° to 115° C. in the same manner as in Example 1 until 27.7 parts of water were formed.

After dissolving the reaction mixture in 1000 parts of toluene, neutralizing the solution with an aqueous 20% solution of sodium hydroxide and washing the thus neutralized solution three times with each 400 parts of an aqueous 20% solution of sodium chloride, the solvent in the solution was distilled off from the solution under a reduced pressure, thereby obtaining 545.6 parts of a pale yellow liquid showing the following properties.

| specific gravity (25° C.) | 1.090 |
|---|---|
| viscosity (25° C.) | 686.4 cps |
| saponification value | 423.5 mgKOH/g |
| acid value | 0.01 mgKOH/g |
| refractive index (20° C.) | 1.4856 |
| Elementary analytical data: | C (%) H (%) |
| | 66.97    8.71 |

The result of NMR measurement:

| No. of Peak | Absorption frequency (Hz) | No. of Peak | Absorption frequency (Hz) |
|---|---|---|---|
| 1 | 11735.1 | 26 | 3003.2 |
| 2 | 11323.1 | 27 | 2970.1 |
| 3 | 9236.5 | 28 | 2915.1 |
| 4 | 8853.1 | 29 | 2899.6 |
| 5 | 8831.1 | 30 | 2809.3 |
| 6 | 8703.3 | 31 | 2789.5 |
| 7 | 8472.0 | 32 | 2725.6 |
| 8 | 5268.3 | 33 | 2663.0 |
| 9 | 5235.2 | 34 | 2633.4 |
| 10 | 5204.4 | 35 | 2593.4 |
| 11 | 4684.4 | 36 | 2306.9 |
| 12 | 4668.9 | 37 | 2254.0 |
| 13 | 4651.3 | 38 | 2212.2 |
| 14 | 4640.3 | 39 | 2196.8 |
| 15 | 4609.4 | 40 | 2190.1 |
| 16 | 4585.2 | 41 | 2088.8 |
| 17 | 4360.5 | 42 | 2057.9 |
| 18 | 4336.2 | 43 | 1919.1 |
| 19 | 4219.5 | 44 | 1886.1 |
| 20 | 3349.1 | 45 | 1857.4 |
| 21 | 3329.3 | 46 | 1727.4 |
| 22 | 3316.1 | 47 | 1707.6 |
| 23 | 3089.1 | 48 | 1663.5 |
| 24 | 3040.6 | 49 | 1238.3 |
| 25 | 3018.6 | 50 | 0.0 |

Of the absorptions shown above, Nos. 8, 9 and 10 are absorption peaks of the solvent.

APPLICATION EXAMPLE 1

The primary irritation index (P.I.I.), the rate of curing and the degree of water absorption of each of the diesters of (meth)acrylic acid produced by the method set forth above are shown in Table 1 while being compared with those of 1,6-hexanediol diacrylate and neopentyl glycol diacrylate.

Methods for Measurements

The measurements were carried out as follows. PII(-primary irritation index)

PII of diesters of (meth)acrylic acid was obtained on the basis of the experiments described in Huntingdon Research Centre Report (Huntingdon Cambs., PE186ES, England).

Outlined Procedure

Six white strain rabbits were used as the test animal, and hair was removed with electric clippers from the dorsolumber region of each rabbit.

A 0.5 ml aliquot of the test substance was applied to the exposed skin site on each animal accoding to patch test method, and the thus treated sites were occluded with an impermeable material such as rubber, cloth, etc. for approximately 24 hours.

After 24 hours of the application of the test substance, the occlusive dressing and patches were removed and the examination of the treated skin sites was made by assessing the dermal reactions on the basis of the numerical scoring system set forth below. The examination was made also after 72 hours of the application of the test substance. Further, the examination was made in the same manner as described above on the abraded skin site on each animal. The skin should be abraded to make minor incisions through the stratum corneum, not through the corium, or bleeding takes place.

The numerical scores for erythema and eschar formation and the numerical scores for oedema formation, at both the 24 and 72 hours readings for both intact and abraded skin sites, were added together and divided by 4 to obtain the numerical score for each animal. The average score of 6 animals was calculated on the basis of 6 numerical scores for each animal. The thus obtained average score is referred to as Primery Irritation Index (PII).

| Numerical Scoring System | Score |
|---|---|
| Erythema and eschar formation | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Oedema formation | |
| No oedema | 0 |
| Very slight oedema (barely perceptible) | 1 |
| Slight oedema (edges of area well defined by definite raising) | 2 |
| Moderate oedema (raised approximately 1 mm) | 3 |
| Severe oedema (raised more than 1 mm and extending beyond the area of exposure) | 4 |

For the details of the above skin irritation test, refer to Draize, John. H., Woodard, Geoffrey and Calvery, Herbert O., "Methods for the Study of Irritation and Toxicity of Substances Applied Topically to the Skin and Mucous Membranes", J. Pharm. & Exp. Ther. 82, 337 (1944).

THE SPEED OF CURING

Each of the novel diesters of (meth)acrylic acid obtained in Examples 1 to 5, 1,6-hexanediol acrylate and neopentyl glycol diacrylate was dissolved in an epoxyacrylate resin obtained by esterifying EPIKOTE ® 828 (an epoxy resin of bisphenol A-type, made by Shell Petrochem. Co.) with acrylic acid, and to each of the thus prepared solutions, DAROCURE ® 1173 (made by Merk Co.) was added as a sensitizer in amount of 3% by weight of the thus dissolved substance. The thus prepared composition was applied onto a sheet of polyvinyl chloride at a thickness of 25 μ with a roll-coater, and the thus coated sheet was irradiated by ultraviolet rays from a high-pressure mercury lamp (made by TOSHIBA Co., 2 kw) at a distance of 8 cm while passing the sheet under the mercury lamp. The speed of curing is expressed by the time (sec) required to lose the wet feeling in a finger.

THE DEGREE OF WATER ABSORPTION

To each of the novel diesters of (meth)acrylic acid obtained in Examples 1 to 5, 1,6-hexanediol diacrylate and neopentyl glycol diacrylate, 5% by weight of a sensitizer (IRUGACURE ® 184, made by CIBA-GEIGY Co.) was respectively added, and the thus prepared composition was poured into a quartz glass container of 3.0 cm (length)×3.0 cm (width)× 0.1 cm (depth). The container was irradiated by ultraviolet rays from a high-pressure mercury lamp and the thus cured composition was immersed in water at 20° C., and after leaving for one week, the increment of the weight of the cured material was measured to calculate the degree of water-absorption of the specimen.

TABLE 1

| No. | Resin (% by weight) | Di(meth)acrylate (% by weight) | PII | Speed of curing (sec) | Degree of water-absorption (%) |
|---|---|---|---|---|---|
| 1 | epoxyacrylate (30) | 1,6-hexanediol diacrylate (70) | 6.2 | 22 | 0.80 |
| 2 | epoxyacrylate (30) | neopentyl glycol diacrylate (70) | 4.96 | 18.5 | 0.71 |
| 3 | epoxyacrylate (30) | diester obtained in Example 1 (70) | 1.5 | 6.7 | 0.50 |
| 4 | epoxyacrylate (30) | diester obtained in Example 2 (70) | 1.6 | 6.7 | 0.45 |
| 5 | epoxyacrylate (30) | diester obtained in Example 3 (70) | 1.2 | 6.7 | 0.28 |
| 6 | epoxyacrylate (30) | diester obtained in Example 4 (70) | — | 10.1 | 0.35 |
| 7 | epoxyacrylate (30) | diester obtained in Example 5 (70) | — | 13.4 | 0.42 |

[Production of Polyurethane (meth)acrylate (A)]

PRODUCTION EXAMPLE 1

Into a 2 l reactor equipped with a stirrer, a temperature controller, a thermometer and a reflux condenser, 253.1 parts of polypropylene glycol (molecular weight of about 2000 and the hydroxy value of 56.1), 251.3 parts of polyester polyol (PLACCEL ® L-220AL, a reaction product of neopentyl glycol, adipic acid and ε-caprolactone, made by DICEL Chem. Ind. Co., Ltd., molecular weight of about 2000 and the hydroxy value of 57.5) and 84.7 parts of isophorone diisocyanate were introduced, and the mixture was heated for 10 hours at a temperature of 80° C. The reaction mixture was cooled to 60° C., and 91.4 parts of ε-caprolactone-ε-hydroxyethyl acrylate (PLACCEL ® FA-2, made by DAICEL Chem. Ind. Co., Ltd.), 0.3 part of methoquinone and 0.1 part of di-n-butyltin dilaurate were added to the reacion mixture, and the thus prepared mixture was heated to from 75° to 80° C. to carry out the reaction until the reaction was completed, the end point being shown by the presence of less than about 0.1% of free isocyanate group. The thus obtained product showed the following physical constants:

| viscosity (60° C.) | 110 poise |
|---|---|
| refractive index (20° C.) | 1.4721 |

PRODUCTION EXAMPLE 2

In a similar reactor as in Production Example 1, 714 parts of polytetramethylene glycol (molecular weight of 2040 and the hydroxyl value of 55.0), 67.6 parts of neopentyl glycol and 444.6 parts of isophorone diisocyanate were introduced, and the content of the reactor was heated at a temperature of 80° C. for 10 hours. Then the reaction mixture was cooled to 60° C. and 239 parts of 2-hydroxyethyl acrylate, 0.7 part of methoquinone, and 0.3 part of di-n-butyltin dilaurate were added to the reaction mixture. The mixture was heated at a temperature of 75° to 80° C. until the reaction was completed, the end point of the reaction being shown by the presence of free isocyanate group of less than about 0.1%. The reaction product showed the following physical constants:

| viscosity (25° C.) | 244 poise |
| refractive index (20° C.) | 1.4792 |

[Preparation of the resin composition]

EXAMPLE A 1

By mixing 40 parts of polyurethane acrylate (A) obtained in Production Example 2, 25 parts of diester of acrylic acid (B) obtained in Example 2, 35 parts of dicyclopentadieneoxyethyl acrylate (FA-512A, made by HITACHI KASEI Co., Ltd.) (C), 5 parts of 1-hydroxycyclohexyl phenyl ketone (IRUGACURE®184, made by Ciba-Geigy Co.) (D) and 0.01 part of methylhydroquinone together, the resin composition A was prepared, the properties thereof and the properties of the cured material thereof being shown in Table 2.

EXAMPLE A 2

The resin composition B was prepared by mixing 10 parts of polyurethane acrylate (A) obtained in Production Example 1, 40 parts of polyurethane acrylate (A) obtained in Production Example 2, 25 parts of the diester of acrylic acid (B) obtained in Example 1, 25 parts of hydrogenated dicyclopentadiene acrylate (FA-513A, made by HITACHI KASEI Co., Ltd.) (C), 3 parts of benzil dimethyl ketal (IRGACURE® 651, made by Ciba-Geigy Co.) (D) and 0.01 part of methylhydroquinone together. The properties of the thus prepared resin composition and those of the cured material thereof are shown in Table 2.

EXAMPLE A 3

The resin composition C was prepared by mixing 35 parts of polyurethane acrylate (A) obtained in Production Example 2, 40 parts of the diester of acrylic acid (B) obtained in Example 3, 10 parts of phenyloxyethyl acrylate (PO-A, made by KYOEI Oil and Fat Co. Ltd.) (C), 15 parts of dicyclopentadieneoxyethyl acrylate (FA-512A, made by HITACHI KASEI Co., Ltd.) (C), 3 parts of benzil dimethyl ketal (D) and 0.01 part of methylhydroquinone together. The properties of the thus prepared resin composition C and those of the cured material thereof are shown in Table 2.

EXAMPLE A 4

By mixing 10 parts of polyurethane acrylate (A) obtained in Production Example 1, 35 parts of polyurethane acrylate (A) obtained in Production Example 2, 25 parts of the diester of acrylic acid (B) obtained in Example 1, 20 parts of hydrogenated dicyclopentadiene acrylate (C), 10 parts of N-vinylpyrrolidone (C), 3 parts of benzil dimethyl ketal (D) and 0.01 part of methylhydroquinone together, the resin composition D was prepared. The properties of the thus prepared resin composition D and those of the cured material thereof are shown in Table 2.

EXAMPLE A 5

By mixing 40 parts of polyurethane acrylate (A) obtained in Production Example 2, 15 parts of the diester of acrylic acid (B) obtained in Example 2, 10 parts of the diester of acrylic acid (B) obtained in Example 3, 15 parts of hydrogenated dicyclopentadiene acrylate (C), 10 parts of N-vinylpyrrolidone (C), 10 parts of tetrahydrofurfuryl acrylate (C), 3 parts of benzyl dimethyl ketal (D) and 0.01 part of methylhydroquinone together, the resin composition E was prepared. The properties of the thus prepared resin composition E and those of the cured material thereof are shown in Table 2.

COMPARATIVE EXAMPLE 1

As the ultraviolet ray-curable, top-coating composition for optical fiber to be compared to the resin composition prepared in Examples A 1 to A 5, DESOTO® 950×042 commercialized by Desoto Chemical Co. was chosen. The properties of DESOTO® 950×042 (referred to as the resin composition F) and those of the cured material thereof are also shown in Table 2 for comparison.

TABLE 2

| | Resin Composition | | | | | |
|---|---|---|---|---|---|---|
| | A | B | C | D | E | F |
| Viscosity of the composition (25° C., cps) | 3300 | 4500 | 2200 | 1600 | 2300 | 18500 |
| Properties of Cured material | | | | | | |
| Hardness (Shore D) | 70 | 60 | 45 | 65 | 60 | 54 |
| Tensile strength (23° C., kg/mm²) | 2.1 | 3.0 | 2.5 | 3.4 | 2.8 | 2.4 |
| Elongation at break (23° C., %) | 56 | 70 | 80 | 75 | 86 | 35 |
| Young's modulus (60° C., kg/mm²) | 1.4 | 3.5 | 2.3 | 6.9 | 1.4 | 2.4 |
| Young's modulus (40° C., kg/mm²) | 9.4 | 18.7 | 10.5 | 26.8 | 6.8 | 6.1 |
| Young's modulus (23° C., kg/mm²) | 22.9 | 30.1 | 25.3 | 47.8 | 31.2 | 15.0 |
| Young's modulus (−20° C., kg/mm²) | 97.9 | 72.1 | 69.1 | 95.7 | 95.2 | 77.1 |
| Degree of water-absorption (increment of weight, %) | 0.9 | 0.7 | 0.4 | 1.6 | 1.9 | 4.7 |

Determination of Shore Hardness D of the cured material

After curing each specimen of the resin compositions A, B, C, D, E and F by irradiating with ultraviolet rays from a high-pressure mercury lamp of 2 kw at a distance of 8 cm under the lamp while moving the composition at a speed of 5 m/min, the specimen was obtained as a sheet of 250 μm in thickness. The shore hardness D of the sheet was determined following the method of Japanese Industrial Standards (JIS) Z 2246.

Determination of Tensile strength (kq/mm²), Elongation at break (%) and Young's modulus (kq/mm²) of the specimen Each sheet of the cured resin compositions A to F made by the same method as above was used for determination of the tensile strength, the elongation at break and the Young's modulus.

Determination of the degree of water-absorption

Each sheet of the cured resin compositions A to F made by the same method as above was immersed in pure water at 20° C. for 24 hours. The difference between the weight after and before immersion of each specimen was measured and the degree of water-absorption was expressed in percentage of the increment of the weight due to the absorbed water.

EXAMPLE A 6

The base material for optical glass fiber was heated to about 2000° C. and spun into the optical glass fibers of 125 μm in the outer diameter at a speed of 5 m/sec, and in the next successive step, a primary coating agent (a mixture of 50% by weight of polyurethane acrylate, 45% by weight of a monoacrylate of 1:1 adduct of tetrahydrofurfuryl alcohol and ε-caprolactone, and 5% by weight of an initiator of photopolymerization) was applied onto the thus spun optical glass fiber, and then the thus applied primary coating was cured by ultraviolet rays. Then, after applying each of the resin compositions A to B obtained in Examples 1 to 5 onto the thus primary-coated optical glass fiber, the thus top-coated optical glass fiber was irradiated by ultraviolet rays from a high-pressure mercury lamp.

Each of the thus obtained optical glass fiber did not show any change of transmission loss at a temperature as low as −60° C.

THE EFFECT OF THE INVENTION

The diesters of (meth)acrylic acid according to the present invention shows a low Primary Irritation Index, has an relatively low viscosity and cures at a high speed.

The resin composition according to the present invention cures at a high speed and has an appropriate viscosity for application, and the resin coating obtained by curing the resin composition according to the present invention is large in elongation and low in water-absorption, and has an appropriate Young's modulus and hardness, namely it is suitable for top-coating of the optical glass fiber for use in transmitting light.

What is claimed is:

1. Diesters of (meth)acrylic acid represented by the formula;

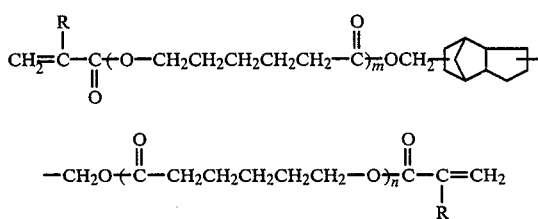

wherein the mean values of m and n are respectively 0 to 5, the mean value of m+n is 1 to 10 and R represents a hydrogen atom or a methyl group.

2. Diesters according to claim 1, wherein R represents a hydrogen atom.

3. Diesters according to claim 1 or 2, wherein the mean values of m and n are respectively 0 to 3 and the mean value of m+n is 1 to 6.

4. Resin compositions comprising polyurethane (meth)acrylate(s) (A), diester(s) of (meth)acrylic acid (B) represented by the formula:

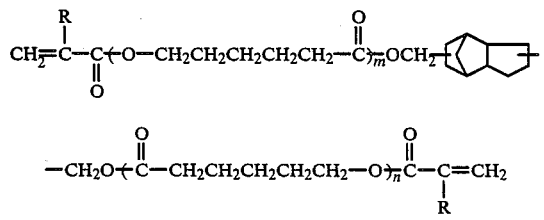

wherein the mean values of m and n are respectively 0 to 5, the mean value of m+n is 1 to 10 and R represents a hydrogen atom or a methyl group, monoethylenically unsaturated monomer(s) (C) and initiator(s) of photopolymerization (D) as an optional component.

5. Resin compositions according to claim 4, comprising 20 to 70% by weight of polyurethane (meth)acrylate(s) (A), 5 to 50% by weight of diester(s) of (meth)acrylic acid (B), 10 to 50% by weight of monoethylenically unsaturated monomer(s) (C) and 0 to 10% by weight of initiator(s) of photopolymerization (D).

6. Resin compositions according to claim 5, wherein the content of said initiator of photopolymerization is 0.1 to 10% by weight.

7. Resin compositions according to claim 5 or 6, wherein R of said diester of (meth)acrylic acid is a hydrogen atom.

8. Resin compositions according to claim 5 or 6, wherein the mean values of m and n are respectively 0 to 3 and the mean value of m+n is 1 to 6.

9. Resin compositions according to claim 4, 5 or 6, wherein the average molecular weight of said polyurethane (meth)acrylate is from 500 to 5000.

10. Resin compositions according to claim 5, comprising 30 to 60% by weight of polyurethane (meth)acrylate(s) (A), 20 to 40% by weight of diester(s) of (meth)acrylic acid (B), 20 to 40% by weight of monoethylenically unsaturated monomer(s) (C), and 1 to 5% by weight of initiator(s) of photopolymerization (D).

11. Resin compositions according to claim 4, further comprising polymerizable monomers selected from the group consisting of polyethylene glycol di(meth)acrylate, polypropylene glycol di(meth)acrylate, trimethylolpropane triacrylate, epoxyacrylate, polyesteracrylate, epoxy resins, polyurethanes, polybutadienes, polyethers, polyamideimides, silicone resins and phenol resins.

12. Resin compositions according to claim 4, wherein said monoethylenically unsaturated monomer(s) are selected from the group consisting of di-cyclopentadieneoxyethyl acrylate, dicyclopentadiene acrylate, hydrogenated-dicyclopentadiene acrylate, isbornyl (meth)acrylate, (meth)acrylate of hydrogenated beta-naphthol, (meth)acrylate of tricyclodecanemethylol, phenyloxyethyl (meth)acrylate, tetrahydrofurfuryl (meth)acrylate, adamantane (meth)acrylate, and N-vinylpyrrolidone.

13. Resin compositions according to claim 4, wherein said initiator(s) of photopolymerization are selected from the group consisting of benzoin ethyl ether, benzoin isobutyl ether, benzoin isopropyl ether, 2, 2-diethoxyacetophenones, 4'-phenoxy-2, 2,2-dichloroacetophenones, 2-hydroxy-2-methdylpropiophenone, 4,'-isopropyl-2-hydroxy-2-methylpropiophenone, 4,'dodecyl-2-hydroxy-2 propiophenone, benzildimethylketal, 1-hydroxycyclohexyl phenyl ketone, 2-ethylanthraquinone, 2-chloroanthraquinone, thioxanthones, and mixtures thereof.

14. Resin compositions according to claim 4, wherein said monoethlenically unsaturated monomer(s) are selected from the group consisting of hydrogenated-dicyclopentadiene acrylate and dicyclopentadieneoxyethyl acrylate.

* * * * *

UNITED STATES PATENT AND TRADEMARK OFFICE
CERTIFICATE OF CORRECTION

PATENT NO. : 4,843,111
DATED : June 27, 1989
INVENTOR(S) : Minoru Yokoshima, Tetsuo Ohkubo, Hideaki Hattori and Masayuki Kiyomoto It is certified that error appears in the above-identified patent and that said Letters Patent is hereby corrected as shown below:

Column 6, line 11 change "isbornyl" to read --isobornyl--.

Column 18, line 39 (claim 12, line 5) change "isbornyl" to read --isobornyl--; Column 18, lines 49-50 (claim 13, lines 5-6) change "4'-phenoxy-2, 2,2-dichloroacetophenones" to read --4'-phenoxy-2,2-dichloroacetophenone--; Column 18, line 51 (claim 13, line 7) change "4,'-isopropyl" to read --4'-isopropyl--; and Column 18, line 52 (claim 13, line 8) change "4,'dodecyl" to read --4'-dodecyl--.

Signed and Sealed this

Fourth Day of September, 1990

Attest:

HARRY F. MANBECK, JR.

*Attesting Officer*      *Commissioner of Patents and Trademarks*